US010993679B2

(12) United States Patent
Shin et al.

(10) Patent No.: US 10,993,679 B2
(45) Date of Patent: May 4, 2021

(54) PORTABLE X-RAY GENERATION DEVICE HAVING ELECTRIC FIELD EMISSION X-RAY SOURCE

(71) Applicants: VATECH Co., Ltd., Gyeonggi-do (KR); VATECH EWOO Holdings Co., Ltd., Gyeonggi-do (KR)

(72) Inventors: Seunghun Shin, Gyeonggi-do (KR); Jinpyo Chun, Gyeonggi-do (KR); Taewoo Kim, Gyeonggi-do (KR)

(73) Assignees: VATECH Co., Ltd., Gyeonggi-do (KR); VATECH EWOO Holdings Co., Ltd., Gyeonggi-do (KR)

(*) Notice: Subject to any disclaimer, the term of this patent is extended or adjusted under 35 U.S.C. 154(b) by 144 days.

(21) Appl. No.: 15/741,237

(22) PCT Filed: Jun. 30, 2016

(86) PCT No.: PCT/KR2016/007075
§ 371 (c)(1),
(2) Date: Dec. 29, 2017

(87) PCT Pub. No.: WO2017/003236
PCT Pub. Date: Jan. 5, 2017

(65) Prior Publication Data
US 2018/0184990 A1    Jul. 5, 2018

(30) Foreign Application Priority Data

Jun. 30, 2015  (KR) .................. 10-2015-0093282
Jun. 30, 2015  (KR) .................. 10-2015-0093293

(51) Int. Cl.
*H05G 1/34* (2006.01)
*H05G 1/06* (2006.01)
(Continued)

(52) U.S. Cl.
CPC .............. *A61B 6/145* (2013.01); *A61B 6/00* (2013.01); *A61B 6/14* (2013.01); *A61B 6/40* (2013.01);
(Continued)

(58) Field of Classification Search
None
See application file for complete search history.

(56) References Cited

U.S. PATENT DOCUMENTS 4,034,251 A    7/1977   Haas
4,210,813 A    7/1980   Akimov et al.
(Continued)

FOREIGN PATENT DOCUMENTS

CN        2662832 Y      12/2004
CN      102347186 A       2/2012
(Continued)

OTHER PUBLICATIONS

"Handheld X-ray System for Intraoral Radiographic Imaging", Operator Manual Manufactured by ARIBEX, Aribex, Inc.
(Continued)

*Primary Examiner* — Christine S. Kim
(74) *Attorney, Agent, or Firm* — IP Legal Services, LLC

(57) ABSTRACT

Disclosed is a portable X-ray generation device, which uses an electric field emission X-ray source, and is thus advantageous in reducing weight and volume and has excellent reliability in X-ray emission performance. The portable X-ray generation device according to the present invention includes an electric field emission X-ray source, which includes a cathode electrode having an electron emitter, an anode electrode having an X-ray target surface, and a gate electrode between the cathode electrode and the anode electrode; and a driving signal generator configured to generate at least three driving signals applied to the cathode
(Continued)

electrode, the anode electrode, and the gate electrode, respectively, by direct current power having a predetermined voltage, wherein the driving signal generator includes a current controller maintaining a tube current between the anode electrode and the cathode electrode to have a constant value during X-ray emission.

15 Claims, 11 Drawing Sheets

(51) Int. Cl.
  *A61B 6/00*  (2006.01)
  *G01T 1/00*  (2006.01)
  *H05G 1/12*  (2006.01)
  *H01J 35/02*  (2006.01)
  *A61B 6/14*  (2006.01)
  *H05G 1/08*  (2006.01)

(52) U.S. Cl.
  CPC .............. *A61B 6/4405* (2013.01); *G01T 1/00* (2013.01); *H01J 35/02* (2013.01); *H01J 35/025* (2013.01); *H05G 1/06* (2013.01); *H05G 1/12* (2013.01); *H05G 1/34* (2013.01); *H05G 1/085* (2013.01)

(56) References Cited

U.S. PATENT DOCUMENTS

| | | | |
|---|---|---|---|
| 4,646,338 A * | 2/1987 | Skillicorn | H01J 35/04 378/110 |
| 4,856,036 A | 8/1989 | Malcolm et al. | |
| 5,077,771 A | 12/1991 | Skillicorn et al. | |
| 6,661,876 B2 * | 12/2003 | Turner | G01N 23/223 378/138 |
| 7,224,769 B2 | 5/2007 | Turner | |
| 7,496,178 B2 * | 2/2009 | Turner | A61B 6/4405 378/101 |
| 7,949,099 B2 | 5/2011 | Klinkowstein et al. | |
| 8,761,343 B2 * | 6/2014 | Jeong | H01J 35/065 378/121 |
| 2005/0018817 A1 | 1/2005 | Oettinger et al. | |
| 2006/0098779 A1 | 5/2006 | Turner | |
| 2007/0230659 A1 | 10/2007 | Turner | |
| 2007/0269010 A1 | 11/2007 | Turner | |
| 2009/0310742 A1 | 12/2009 | Kim et al. | |
| 2011/0074309 A1 | 3/2011 | Jeong et al. | |
| 2011/0280371 A1 | 11/2011 | Molloi et al. | |
| 2011/0286581 A1 | 11/2011 | Sprenger et al. | |
| 2011/0305312 A1 | 12/2011 | Hu | |
| 2012/0027177 A1 | 2/2012 | Ogata et al. | |
| 2012/0027179 A1 | 2/2012 | Ogata et al. | |
| 2012/0148027 A1 | 6/2012 | Jeong et al. | |
| 2013/0003923 A1 | 1/2013 | Sackett | |
| 2013/0114794 A1 | 5/2013 | Yamamoto | |
| 2013/0271037 A1 | 10/2013 | Jeong et al. | |
| 2013/0336461 A1 * | 12/2013 | Jeong | H01J 35/14 378/138 |
| 2014/0023178 A1 | 1/2014 | Kim et al. | |
| 2014/0205060 A1 | 7/2014 | Kim et al. | |
| 2014/0346975 A1 * | 11/2014 | Jeong | H01J 1/304 315/308 |
| 2015/0071413 A1 * | 3/2015 | Kim | H01J 9/445 378/207 |
| 2015/0098551 A1 | 4/2015 | Kwak et al. | |
| 2015/0342558 A1 | 12/2015 | Kwak et al. | |
| 2017/0076903 A1 * | 3/2017 | Turner | H01J 35/06 |
| 2017/0135189 A1 * | 5/2017 | Jeong | A61B 6/00 |
| 2017/0347438 A1 * | 11/2017 | Kang | H05G 1/34 |
| 2018/0078229 A1 | 3/2018 | Wang | |
| 2019/0242834 A1 | 8/2019 | Rothschild et al. | |

FOREIGN PATENT DOCUMENTS

| | | |
|---|---|---|
| CN | 102347187 A | 2/2012 |
| CN | 103260325 A | 8/2013 |
| CN | 103906333 A | 7/2014 |
| CN | 104411080 A | 3/2015 |
| JP | 2003-190150 A | 7/2003 |
| JP | 2005-243331 A | 9/2005 |
| JP | 2008-226783 A | 9/2008 |
| KR | 10-2008-0091526 A | 10/2008 |
| KR | 10-2008-0098103 A | 11/2008 |
| KR | 10-2009-0053568 A | 5/2009 |
| KR | 10-2011-0012585 A | 2/2011 |
| KR | 10-2011-0033762 A | 3/2011 |
| KR | 10-2012-0064783 A | 6/2012 |
| KR | 10-2012-0097563 A | 9/2012 |
| KR | 10-2012-0120849 A | 11/2012 |
| KR | 10-2013-0058162 A | 6/2013 |
| KR | 10-2013-0084257 A | 7/2013 |
| KR | 10-2013-0115978 A | 10/2013 |
| KR | 10-2014-0013403 A | 2/2014 |
| KR | 10-2015-0031395 A | 3/2015 |
| WO | 2009/151197 A1 | 12/2009 |
| WO | 2013/005871 A1 | 1/2013 |
| WO | 2013/131628 A1 | 9/2013 |
| WO | 2015/053544 A1 | 4/2015 |

OTHER PUBLICATIONS

European Patent Office, European Search Report of EP Patent Application No. 16818270.7, dated Jan. 28, 2019.

European Patent Office, European Search Report of EP Patent Application No. 16818269.9, dated Jan. 28, 2019.

European Patent Office, European Search Report of corresponding EP Patent Application No. 16818269.9, dated Jun. 21, 2019.

State Intellectual Property Office of People's Republic of China, Office Action of corresponding CN Patent Application No. 201680049616.5, dated Feb. 28, 2019.

State Intellectual Property Office of People's Republic of China, Office Action of corresponding CN Patent Application No. 201680049616.5, dated Nov. 19, 2019.

State Intellectual Property Office of People's Republic of China, Office Action of corresponding CN Patent Application No. 201680049619.9, dated Feb. 28, 2019.

State Intellectual Property Office of People's Republic of China, Office Action of corresponding CN Patent Application No. 201680049619.9, dated Nov. 19, 2019.

Joel E. Gray et al., "Dental Staff Doses With Handheld Dental Intraoral X-Ray Units", Health Physics, Feb. 2012, pp. 137-142, vol. 102, No. 2.

Wu Guangning, Electrified Railway High Voltage Project, Section 2 DC High Voltage Test, China Railway Press, May 31, 2011, pp. 72-77.

Anirban Basu et al., "A portable x-ray source with a nanostructured Pt-coated silicon field emission cathode for absorption imaging of iow-Z materials", Journal of Physics D: Applied Physics, May 6, 2015, vol. 48, pp. 1-11.

* cited by examiner

000# PORTABLE X-RAY GENERATION DEVICE HAVING ELECTRIC FIELD EMISSION X-RAY SOURCE

CROSS REFERENCE TO RELATED APPLICATIONS

This application is a National Stage Patent Application of PCT International Patent Application No. PCT/KR2016/007075 (filed on Jun. 30, 2016) under 35 U.S.C. § 371, which claims priority to Korean Patent Application Nos. 10-2015-0093293 (filed on Jun. 30, 2015), and 10-2015-0093282 (filed on Jun. 30, 2015), the teachings of which are incorporated herein in their entireties by reference.

TECHNICAL FIELD

The present invention relates generally to a portable X-ray generation device. More particularly, the present invention relates to a portable X-ray generation device that is reduced in size and suitable for intra-oral X-ray imaging in dentistry by using an electric field emission X-ray source.

BACKGROUND ART

X-ray imaging is a radiography method using straightness and attenuation of X-rays, and based on the amount of attenuation accumulated in the course of the X-rays passing through an imaging area, it provides an X-ray image of the internal structure of the imaging area. To achieve this, an X-ray imaging system includes: an X-ray generation apparatus configured to irradiate X-rays to a imaging area; an X-ray sensor disposed to face the X-ray generation apparatus with the imaging area therebetween, and configured to detect X-rays that have penetrated through the imaging area; and an image processing apparatus configured to construct a gray-level X-ray image of an internal structure of the imaging area by using X-ray projection data, as a detection result detected by the X-ray sensor.

In recent years, X-ray imaging has been rapidly evolving into DR (Digital Radiography) using digital sensors due to the development of semiconductor and information processing technologies, whereby image processing technology has also been developed and is used in various ways according to the purpose and application field. As an example, there is intra-oral X-ray imaging mainly used in dentistry. Intra-oral X-ray imaging is an X-ray imaging technology for obtaining an X-ray image of a limited imaging area of a subject, and is performed as follows: an X-ray sensor is placed inside the subject's mouth; and X-rays are irradiated from an X-ray generation apparatus outside the mouth to the X-ray sensor, thereby obtaining an X-ray image of a tooth and surrounding tissue that is disposed between the X-ray generation apparatus and the X-ray sensor. The intra-oral X-ray image has advantages of low distortion, excellent resolution and sharpness, and relatively low radiation exposure, so it is mainly used for implant treatment or endodontic treatment requiring high resolution.

Meanwhile, an X-ray imaging device for intra-oral X-ray imaging is generally called a portable X-ray generation device, and X-ray imaging is often performed by a user holding the device. In order to improve the usability and accuracy of intra-oral X-ray imaging and to improve the utilization thereof, it is required to reduce the weight and size of the X-ray generation device.

In recent years, to reduce the size of the X-ray generation device, research on an electric field emission X-ray source using a nanostructure such as a carbon nanotube (CNT) has been conducted. The X-ray source using the carbon nanotube is an electric field emission type, and differs from a conventional tungsten filament based hot cathode X-ray source in its electron emission mechanism. Since the carbon nanotube-based X-ray source can emit electrons with low power and emit electrons along the length of the carbon nanotube, X-ray emission efficiency is very high due to excellent directivity of electrons toward the X-ray target surface at the anode electrode. Further, it is easy to emit X-rays in pulse shape and it is possible to take an X-ray movie, whereby it is very likely to be used for dental diagnosis, especially intra-oral X-ray imaging.

A conventional field emission X-ray source includes an electron emitter disposed on a cathode electrode in a vacuum container, and a gate electrode disposed adjacent to the electron emitter, wherein electrons are emitted by an electric field formed between the gate electrode and the electron emitter. The gate electrode is in a meshed shape or a metal plate in which a plurality of holes is arranged according to an array of the electron emitter. When the electron beam emitted from the electron emitter travels through this mesh structure or the plurality of holes, the electrons are accelerated by an electric field formed between the anode and the cathode so as to strike an X-ray target surface provided on the anode side so that X-rays are emitted. Further, a focusing electrode disposed around the electron beam traveling path between the cathode and the anode may be provided to form an electric field for focusing the electron beam.

The electric field emission X-ray source is advantageous in downsizing and reducing weight of the X-ray generation device. However, since a high potential difference of about several tens of kV is formed between the anode and the cathode, a small sized device is at risk of dielectric breakdown. In order to increase the insulation stability, it is possible to increase the insulation distance or to add an insulating structure, but this may be disadvantageous in downsizing and reducing weight of the device.

DISCLOSURE

Technical Problem

Accordingly, the object of the present invention is to provide a portable X-ray imaging device having an electric field emission X-ray source with improved user friendliness, operational stability, and reliability. More particularly, an object of the present invention is to provide a portable X-ray imaging device with improved reliability, in which an electric field emission X-ray source is applied to the device, the device is driven by using driving signals of at least three voltage levels, external power and a battery are available, the amount of X-rays per unit time is maintained constant during X-ray emission, and although the high voltage of several tens of kV is used, the insulation performance of the driving circuit as well as the electric field emission X-ray source is excellent.

Further, another object of the present invention is to maintain the tube current value between the anode electrode and the cathode electrode constant while the gate ON voltage is applied in generating driving signals applied to the electric field emission X-ray source, such that the emitted X-ray output is maintained constant.

Meanwhile, a further object of the present invention is to provide a portable X-ray generation device light in weight compared to an X-ray emission output thereof by having a structure that provides high insulation stability and is advantageous in downsizing and reducing weight of the device.

Technical Solution

In order to achieve the above object, according to some aspects of the present invention, there is provided a portable X-ray generation device including: an electric field emission X-ray source including a cathode electrode having an electron emitter, an anode electrode having an X-ray target surface, and an gate electrode disposed between the cathode electrode and the anode electrode; and a driving signal generator configured to generate at least three driving signals applied to the cathode electrode, the anode electrode, and the gate electrode, respectively, by using direct current power having a predetermined voltage.

The driving signal generator may include a voltage converter configured to generate a first driving voltage of a first voltage level V1 for the anode electrode, a second driving voltage of a second voltage level V2 for the gate electrode, and a third driving voltage of a third voltage level V3 for the cathode electrode by using the direct current power, and the first to third voltage levels V1, V2, and V3 may have relations of V1>V2>V3.

Further, a voltage of the direct current power may be 5V to 30V, the first driving voltage may have a potential difference of 55 kV to 75 kV for the third driving voltage, and the second driving voltage may have a potential difference of 0.5 kV to 20 kV for the third driving voltage.

In this case, the electric field emission X-ray source may further include a focusing electrode disposed between the gate electrode and the anode electrode, the driving signal generator may further generate a fourth driving voltage for the focusing electrode to apply the same to the focusing electrode, and the fourth driving voltage may have a potential difference of 0.5 kV to 20 kV for the third driving voltage.

Meanwhile, the driving signal generator may include: a first voltage converter configured to generate the second driving voltage by firstly boosting a voltage of the direct current power to the second voltage level V2; and a second voltage converter configured to generate the first driving voltage by secondly boosting the second voltage level to the first voltage level V1. Here, the first voltage converter may include a coil transformer, and the second voltage converter may include a voltage multiplier circuit using a plurality of diodes and a capacitor.

Meanwhile, the portable X-ray generation device may further include: a first insulation molding configured to surround a part or all of the electric field emission X-ray source and also serve as an X-ray shielding layer; a printed circuit board with the electric field emission X-ray source mounted thereto; and a second insulation molding configured to surround parts or all of the electric field emission X-ray source with the first insulation molding and the printed circuit board. In this case, the driving signal generator may include: a first voltage converter configured to generate a second driving voltage of a second voltage level V2 by firstly boosting a voltage of the direct current power; and a second voltage converter configured to generate a first driving voltage of a first voltage level V1 by secondly boosting the second voltage level, wherein the second voltage converter is mounted to the printed circuit board, and the second insulation molding surrounds a part or all of the second voltage converter.

In the portable X-ray generation device, the driving signal generator may include a current controller configured to maintain a tube current between the anode electrode and the cathode electrode to have a constant value during X-ray emission.

The current controller may adjust a voltage of the driving signal applied to the gate electrode according to the difference between a feedback signal of the tube current value and a set value.

Further, the current controller may include at least one field effect transistor configured to be connected to the cathode electrode and maintain a current value applied during X-ray emission constant. In this case, the driving signal generator may be configured to sequentially turn on the driving signal for the anode electrode and the driving signal for the gate electrode in a state where an ON signal is applied to a gate terminal of the field effect transistor of the current controller.

Meanwhile, the portable X-ray generation device may further include: a main body with the electric field emission X-ray source and the driving signal generator mounted thereto; and a grip rotatably and tiltably coupled to a side of the main body via a freely rotating joint. In this case, the portable X-ray generation device may further include a battery accommodated in the grip and configured to supply the direct current power, and may further include an external power adapter configured to supply the direct current power.

Meanwhile, the portable X-ray generation device may further include: a main body with the electric field emission X-ray source and the driving signal generator mounted thereto; and a holder rotatably and tiltably coupled to a side of the main body via a freely rotating joint.

Meanwhile, the portable X-ray generation device may further include: a main body with the electric field emission X-ray source and the driving signal generator mounted thereto; and an X-ray sensor connected with the main body via a cable and configured to provide imaging data by receiving X-rays emitted from the electric field emission X-ray source and transmitted through a subject. In this case, the portable X-ray generation device may further include a wireless communication module configured to wirelessly transmit the imaging data of the X-ray source or image data obtained by reconstructing the imaging data.

Advantageous Effects

According to the present invention configured as describe above, there is provided a portable X-ray imaging device having an electric field emission X-ray source with improved user friendliness, operational stability, and reliability. More particularly, there is provided a portable X-ray imaging device with improved reliability, in which an electric field emission X-ray source is applied to the device, the device is driven by using driving signals of at least three voltage levels, external power and a battery are available, the amount of X-rays per unit time is maintained constant during X-ray emission, and although the high voltage of several tens of kV is used, the insulation performance of the driving circuit as well as the electric field emission X-ray source is excellent.

Further, according to the present invention, the tube current value between the anode electrode and the cathode electrode is maintained constant while the gate ON voltage is applied in generating driving signals applied to the electric field emission X-ray source, such that the emitted X-ray output is maintained constant.

Meanwhile, according to the present invention, it is advantageous in that since it has a structure small in size and light in weight while providing high insulation stability, it is possible to provide a portable X-ray generation device light in weight compared to an x-ray emission output thereof.

MODE FOR INVENTION

Figure 1:
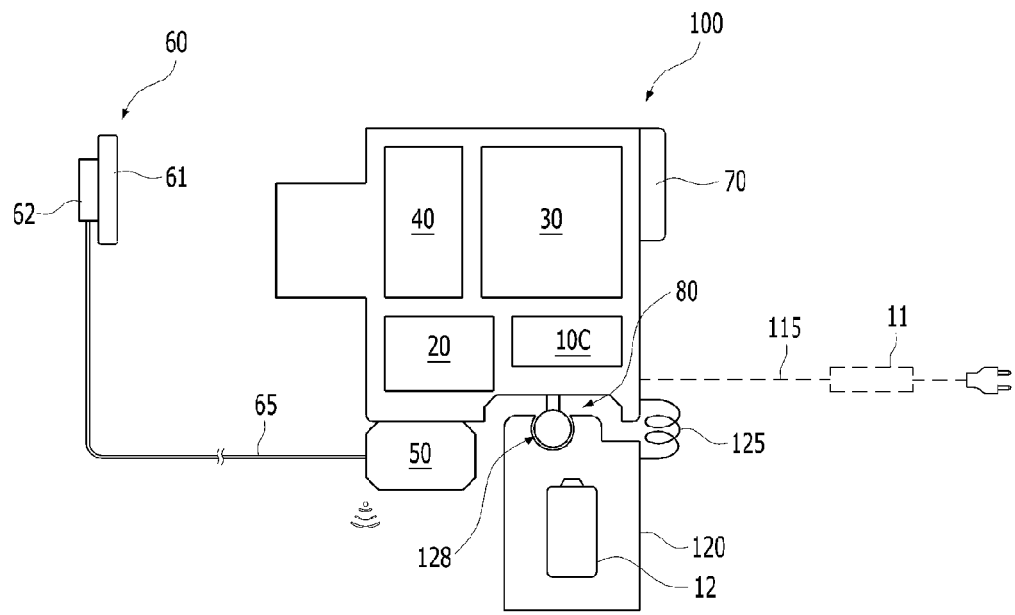
FIG. 1 schematically shows a configuration of a portable X-ray generation device according to an embodiment of the present invention.

Hereinafter, various embodiments of the present invention will be described with reference to the accompanying drawings. The technical idea of the present invention will be understood more clearly by the embodiments. The present invention is not limited to the embodiments described hereinbelow. The same reference numerals are used to designate the same or similar components, and a description of components having the same reference numerals as those described in any one of the drawings may be omitted.

FIG. 1 schematically shows a configuration of a portable X-ray generation device according to an embodiment of the present invention.

The portable X-ray imaging device according to the embodiment is roughly constituted by an X-ray generation device 100 provided with an X-ray source unit 40 to emit X-rays toward a subject, and an X-ray sensor unit 60 configured to generate imaging data by receiving the X-rays transmitted through the subject. The X-ray generation device and the X-ray sensor unit may be connected to each other via a cable 65.

Firstly, to be more specific, the X-ray generation device 100 includes: a power supply unit 10C supplying direct current power having a predetermined voltage by being supplied with power from a battery 12 or an external power adapter 11; a main controller 20 configured to control the entire device according to the user's manipulation; and a driving signal generator 30 configured to provide driving signals of at least three voltage levels to an electric field emission X-ray source mounted to the X-ray source unit 40, by using the direct current power having the predetermined voltage supplied from the power supply unit 10C. Further, the X-ray generation device 100 may be provided with a display 70 configured to display the operating state of the device and input information of the user, and may be provided with a wireless communication module 50 configured to wirelessly transmit imaging data transmitted from the X-ray sensor unit 60 via the cable 65 or image data obtained by reconstructing the imaging data into an X-ray image in the main controller 20 to an external device. The image data reconstructed in the main controller 20 may be displayed as an image through the display 70.

A battery unit 120 provided with the battery 12 may be formed in a detachable grip. Further, the battery unit 120 also serving as a grip may be coupled through a freely rotating joint 80 and 128 so as to be rotatable and tiltable in all directions with respect to a main body of the X-ray generation device 100. The freely rotating joint 80 and 128 may include, for example, a ball 80 provided at a side of the main body, and a ball seat 128 provided at a side of the battery unit 120. The ball and the ball seat may be arranged in opposite positions. Meanwhile, the battery 12 may be electrically connected to the power supply unit 10C, for an example, via a flexible connection cable 125, or, for an example, through a pair of terminal electrodes formed on a part of the freely rotating joint.

The power supply unit 10 is configured to supply the direct current power having the predetermined voltage to the main controller 20 and the driving signal generator 30 by using the power supplied from the battery 12 of the battery unit 120 or the power supplied from the external power adapter 11 indicated by a dotted line in the drawing through a power cable 115. The predetermined voltage may be 5V to 30V, for example, it may be 24V, 12V, or another voltage. Herein, the term power supply unit 10C is functionally used as a concept that encompasses the battery or the external power adapter 11, but in terms of practical placement, the battery 12 is disposed in the grip-battery unit 120 and the external power adapter 11 is also disposed outside the device and connected separately, and only a power supply circuit is disposed inside the device. Meanwhile, when charging the battery 12, the battery unit 120 may be connected directly to the power cable 115 of the external power adapter 11, or via the power supply circuit in the main body of the X-ray generation device 100.

The X-ray sensor unit 60 includes; a sensor portion 61 having a sensor array for receiving X-rays; and a connection portion 62, which connects the sensor portion 61 and the cable 65 together through a plurality of channels, connected in two or more different directions. A detailed description of the X-ray sensor 60 will be made hereinafter, with reference to separate drawings.

Figure 2:
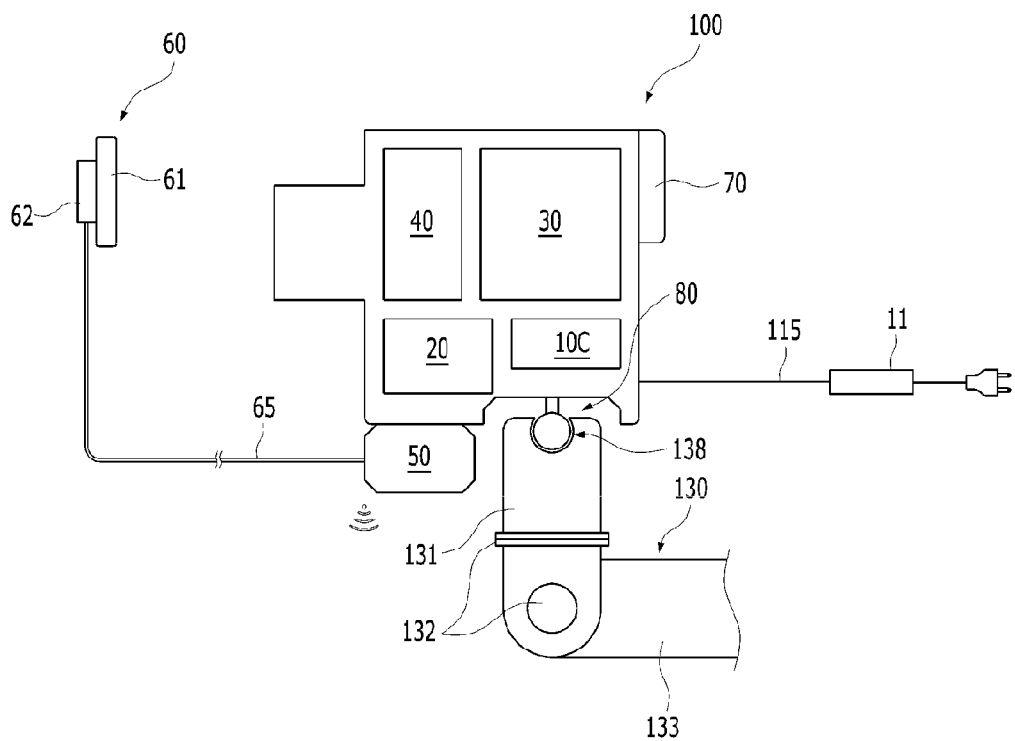
FIG. 2 schematically shows a configuration of the portable X-ray generation device according to an embodiment of the present invention.

FIG. 2 schematically shows a configuration of the portable X-ray generation device according to an embodiment of the present invention.

As shown in the drawing, the portable X-ray imaging device according to the embodiment may be used by being coupled to a holder 130 instead of the battery unit 120 shown in FIG. 1. The holder 130 may be, for example, a standard arm having plurality of arms 133 and a rotation shaft 132, which helps change position, direction, or posture angle of the X-ray generation device 100 while supporting the load thereof. As an example of a simpler form, the holder 130 may be a structure supported on a floor, such as a camera tripod, or a structure supported on a dental unit chair. In any case, a coupling end portion 131 of the holder 130 may be coupled to the X-ray generation device 100 via a freely rotating joint 80 and 138 so as to be rotatable and tiltable in all directions with respect to the X-ray generation device. The freely rotating joint 80 and 138 may include, for example, the ball 80 provided at a side of the main body, and a ball seat 138 provided at a side of the coupling end portion 131 of the holder 130. The ball and the ball seat may be arranged in opposite positions.

Meanwhile, when the holder 130 supersedes the battery unit 120 shown in FIG. 1, it is connected to the external power adapter 11 for power supply. The external power adapter 11 converts the normal commercial AC power to direct current power and supplies the same to the power supply circuit of the power supply unit 10C.

Figure 3:
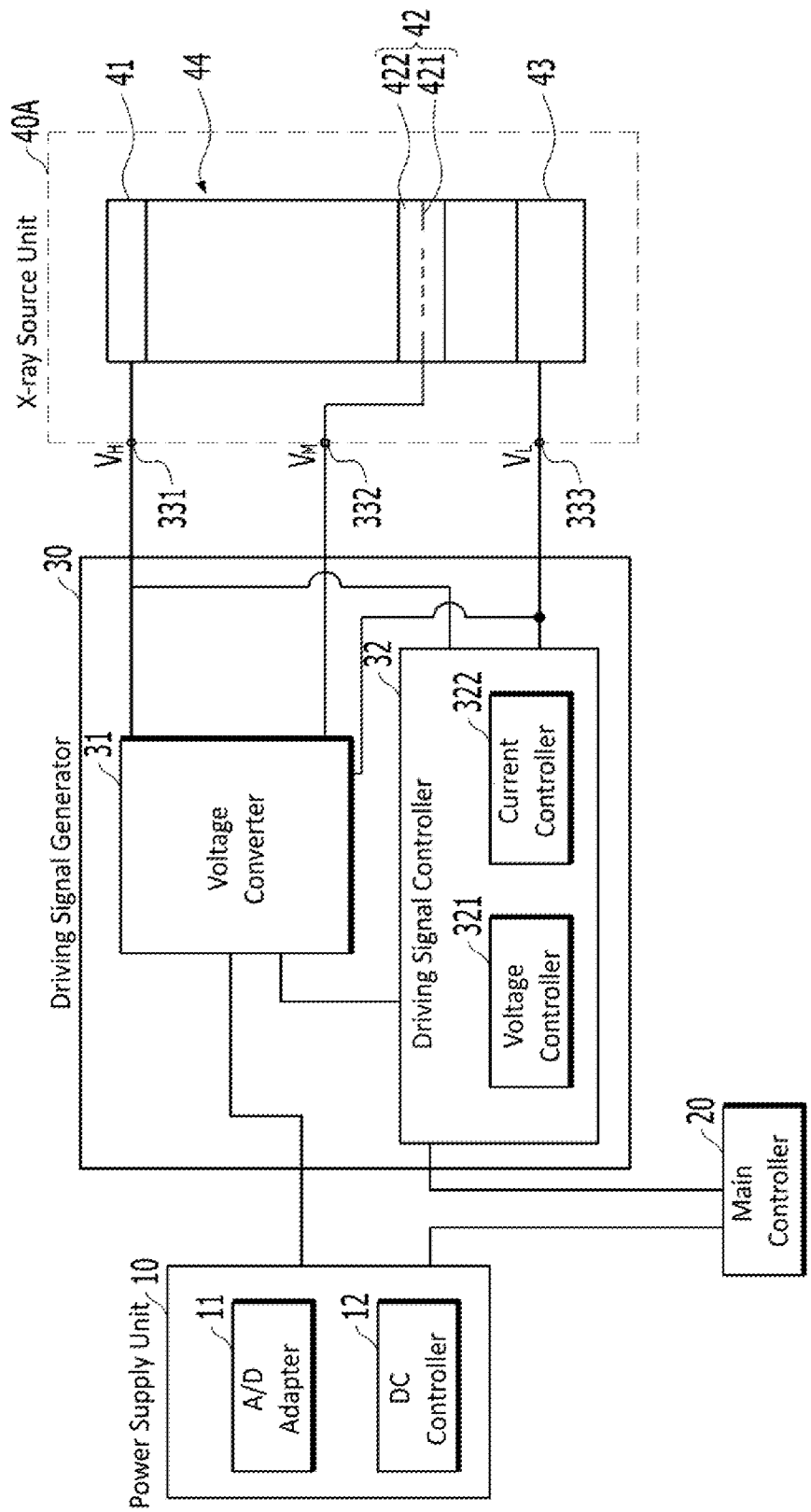
FIG. 3 shows a block diagram of a configuration of the portable X-ray generation device according to an embodiment of the present invention.

FIG. 3 shows a block diagram of a configuration of the portable X-ray generation device according to an embodiment of the present invention.

As described above, the X-ray generation device includes the power supply unit 10 supplying the direct current power having a predetermined voltage, the main controller 20, the driving signal generator 30, and an X-ray source unit 40A.

The X-ray source unit 40A is provided with an electric field emission X-ray source 44. The electric field emission X-ray source 44 includes a cathode electrode 43 having an electron emitter, an anode electrode 41 having an X-ray target surface, and a gate electrode 42. The X-ray source unit 40A may include a printed circuit board with the electric field emission X-ray source 44 mounted thereto, wherein the printed circuit board may be provided with three input terminals connected to the three electrodes 41, 42, and 43, respectively. Meanwhile, the gate electrode 42 may include: a plane portion 421 being in the form of a thin metal plate or a metal mesh having a plurality of holes formed therein so that an electron beam can pass therethrough; and a focusing portion 422 forming a focusing field by an edge connected to the plane portion 421 extending in the longitudinal direction. According to the embodiment, the focusing portion 422 has a band shape extending from the edge of the plane portion 421 in the longitudinal direction thereof in parallel with the outer circumferential surface of a tubular vacuum container forming the body of the electric field emission X-ray source 44.

A positive voltage is applied to the gate electrode 42 to cause electron emission from the electron emitter disposed at the cathode electrode 43, and the electron beam is focused toward the center of the tubular vacuum container, simultaneously. Even though the voltage VM applied to the gate electrode 42 is a positive voltage of several kV, which is considerably lower than the voltage VH of several tens of kV applied to the anode electrode 41, a so-called focusing field is formed between the anode electrode 41 and the inner surface of the focusing portion 422 so that the equipotential surface faces the center thereof.

According to the embodiment, to drive the electric field emission X-ray source 44, a first high voltage VH as a first driving voltage is applied to the anode electrode 41, a second high voltage VM as a second driving voltage is applied to the gate electrode 42, and a driving signal of a low voltage VL as a third driving voltage is applied to the cathode electrode 43. Herein, assuming that the low voltage VL is a reference potential, the first high voltage VH may have a potential difference of 55 kV to 75 kV for the reference potential, as a specific example, a potential difference of 60 kV to 65 kV, and the second high voltage VM may have a potential difference of 0.5 kV to 20 kV for the reference potential, as a specific example, a potential difference of about 10 kV. In other words, assuming that the first high voltage VH, the second high voltage VM, and the low voltage VL are the first to the third voltage levels V1, V2, and V3, the following relationship is established: the first voltage level V1>the second voltage level V2>the third voltage level V3, and the potential difference therebetween is as described above. When the driving signal is applied to each electrode, the electron beam is sufficiently accelerated to collide with the X-ray target surface of the anode electrode 41 to emit X-rays.

The driving signal generator 30 includes: a voltage converter 31 configured to be supplied with the direct current power having a predetermined voltage from the power supply unit 10 and convert the same; and a driving signal controller 32 configured to control operations of the voltage converter 31 by receiving a control signal from the main controller 20. The power supply unit 10 supplies the direct current power of 5V to 30V, specifically, of 24V, to the driving signal generator 30, and to achieve this, the power supply unit may include one or all of the adapter 11 converts external AC power to direct current power, and the battery 12 that is direct current power. The adapter 11 may convert AC power of 100V to 250V into the direct current power of the above mentioned voltage. Further, the power supply unit may include a circuit for selecting an appropriate power depending on the connection or charge state of these power.

The driving signal controller 32 controls the voltage converter 31 to generate the driving signals of the first high voltage VH, the second high voltage VM, and the low voltage VL by using the direct current power to supply the same output terminals 331, 332, and 333, respectively. The driving signal controller 32, for example, provides set values for generating the driving signals of the three voltage levels or provides a switching signal necessary to convert DC to AC for voltage conversion. Further, the driving signal controller 32 includes a voltage controller 321 that feeds back the first high voltage VH and/or the second high voltage VM signal, which is an output driving signal, and controls the voltage to be outputted according to the control purpose.

Further, the driving signal controller 32 according to the embodiment includes a current controller 322 configured to maintain a tube current between the anode electrode 41 and the cathode electrode 43, that is, a current value between the output terminal 331 of the first high voltage VH and the output terminal 333 of the low voltage VL to be constant while ON signals are applied to the anode electrode 41 and the gate electrode 42, i.e., the driving signals of the first high voltage VH and the second high voltage VM are applied. Since the amount of emitted X-rays, more specifically, the amount of X-rays per unit time, is proportional to the tube current value under the assumption that a sufficient potential difference for the acceleration of the electron beam is formed between the cathode electrode 43 and the anode electrode 41, it is possible to control the amount of emitted X-rays to be constant by maintaining the value of the tube current constant. The current controller 322 may actually be implemented in several types of circuits, some of which are described below with some implementation examples.

Figure 4:
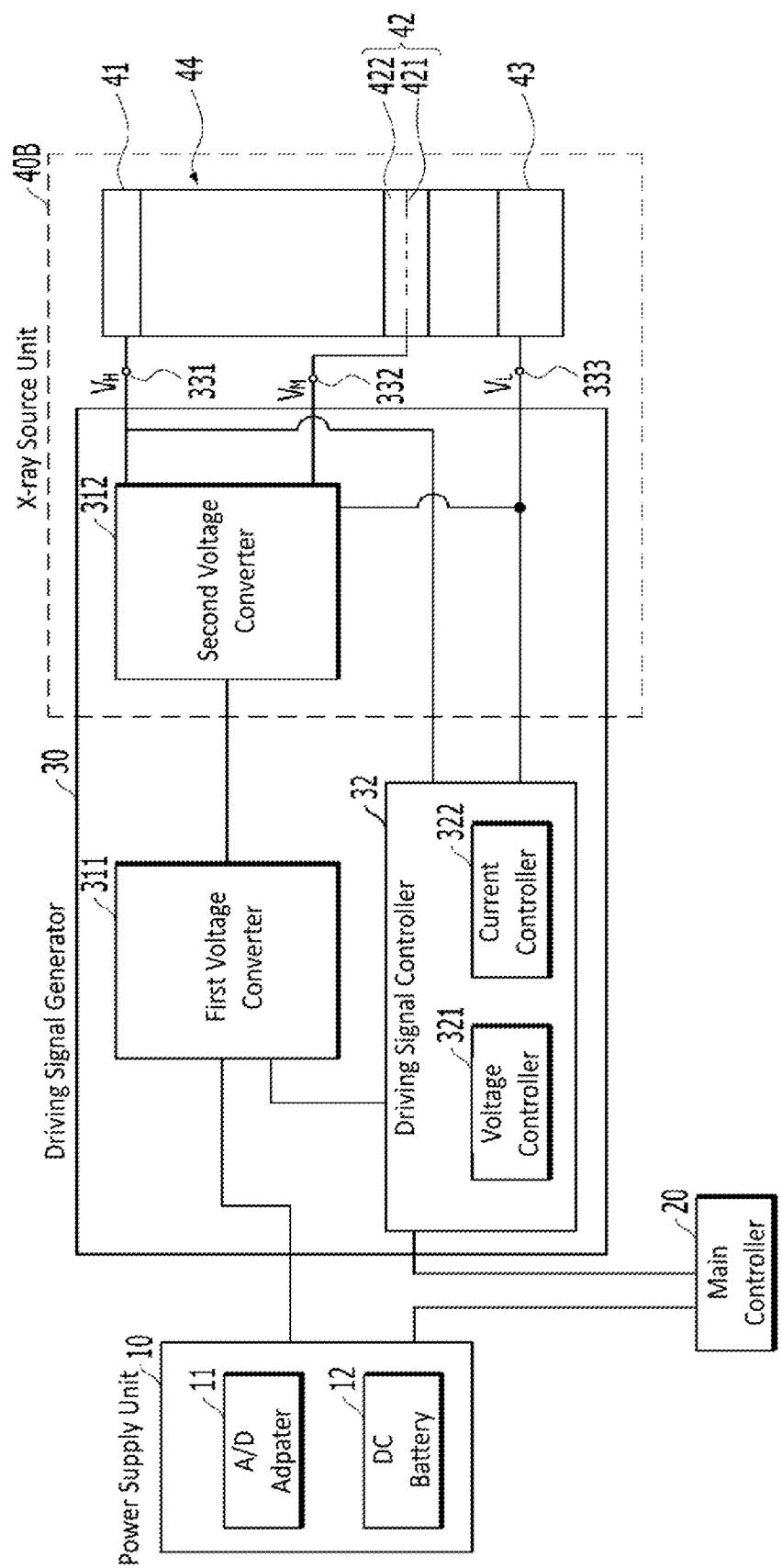
FIG. 4 shows a block diagram of a configuration of the portable X-ray generation device according to an embodiment of the present invention.

FIG. 4 shows a block diagram of a configuration of the portable X-ray generation device according to an embodiment of the present invention.

The configuration of the X-ray generation device according to the embodiment is different from the embodiment of FIG. 3 in that it is configured such that a voltage converter constituting the driving signal generator 30 includes a first voltage converter 311 handling a low voltage, and a second voltage converter 312 handling a high voltage.

Herein, the first voltage converter 311 and the second voltage converter 312 are mounted to different printed circuit boards. For example, the second voltage converter 312 may be mounted to a printed circuit board constituting an X-ray source unit 40B with the X-ray source mounted thereto. For example, the first voltage converter 311 may include a circuit that converts DC to AC for step-up or a voltage step-up circuit that does not require special insulation measures, and the second voltage converter 312 may include a high voltage transformer that boosts the voltage to a high voltage of several kV to several tens of kV, and a regulator circuit that converts high voltage AC into direct current again.

As described above, when the parts handling the high voltage are disposed in the X-ray source unit 40B as the separate second voltage converter 312, it is advantageous in that the insulation measures for the high voltage can be shared with the electric field emission X-ray source 44. The electric field emission X-ray source 44 requires insulation measures to prevent dielectric breakdown between the anode electrode 41 applied with the first high voltage VH of several tens of kV and the cathode electrode applied with the low voltage VL of 0V or grounded voltage, and between the gate electrode 42 applied with the second high voltage VM of several kV and the cathode electrode 43, which is because there is also a risk of dielectric breakdown in the voltage step-up circuit generating the above-mentioned first and second high voltage level driving signals in the voltage converter. According to the embodiment, by disposing the second voltage converter 312 handling the high voltage signals in the X-ray source unit 40B, it is possible to reinforce dielectric strength along with the electric field emission X-ray source 44.

Figure 5:
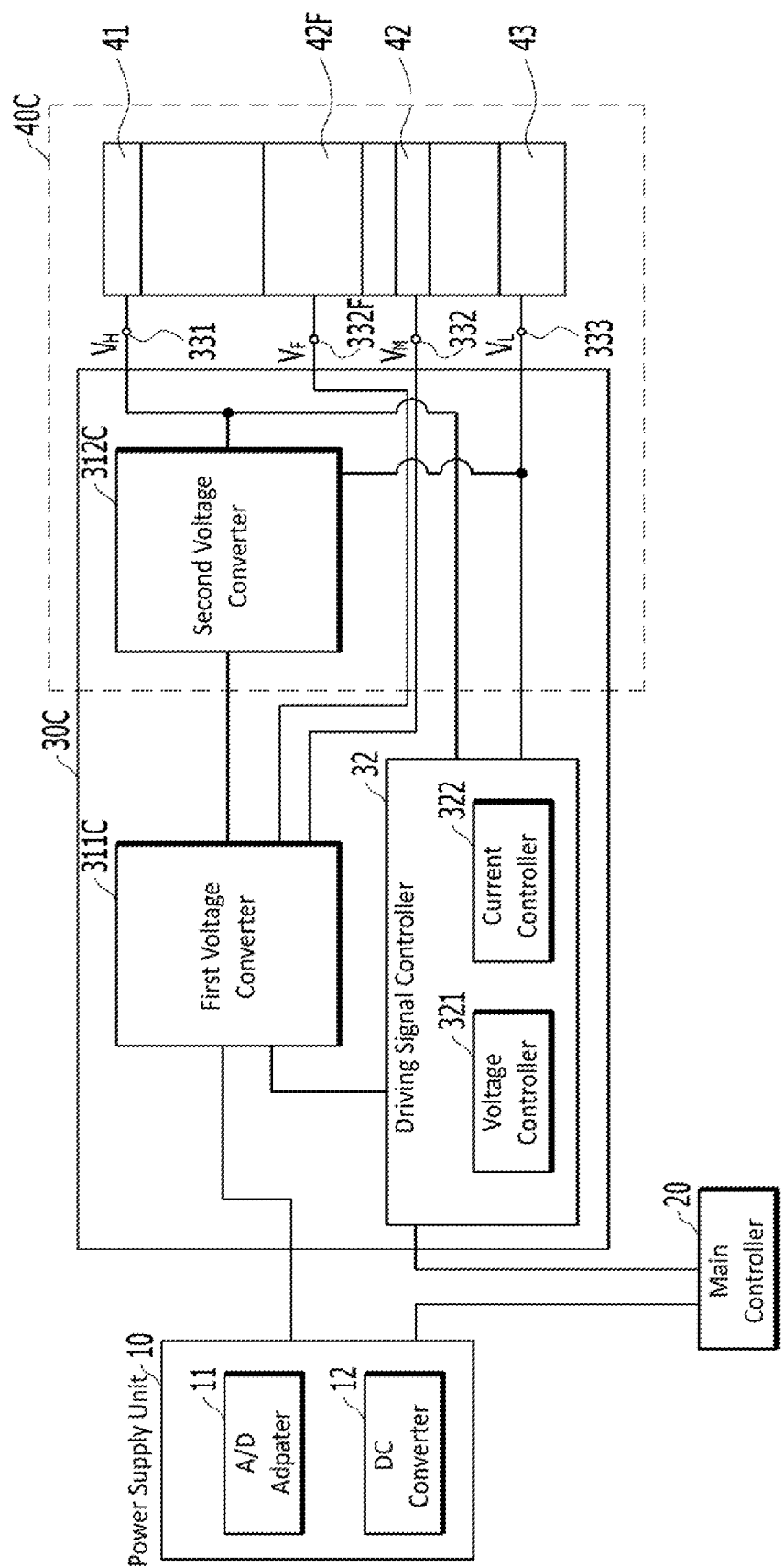
FIG. 5 shows a block diagram of a configuration of the portable X-ray generation device according to an embodiment of the present invention.

FIG. 5 shows a block diagram of a configuration of the portable X-ray generation device according to an embodiment of the present invention.

The configuration of the X-ray generation device according to the embodiment has in common with the embodiment of FIG. 4 that it is configured a voltage converter constituting the driving signal generator 30C includes a first voltage converter 311C handling a low voltage, and a second voltage converter 312C handling a high voltage. The first voltage converter 311C and the second voltage converter 312C may be mounted to the same printed circuit board, or to different printed circuit boards.

The embodiment is different from the embodiment of FIG. 4 in that it is configured such that the first driving voltage generated from the first voltage converter 311C can be used as an input to the second voltage converter 312C, and also used as the second high voltage VM applied directly to the gate electrode 42. To achieve this, the first voltage converter 311C may include a circuit that boosts the voltage to have a potential difference of, for example, about 10 kV based on the low voltage VL.

Meanwhile, in an X-ray source unit 40C according to the embodiment, a focusing electrode 42F functioning to focus the X-ray beam may be provided separately from the gate electrode 42. In this case, the first driving voltage generated in the first voltage converter 311C may be also applied to a terminal 332F connected to the focusing electrode 42F as a third high voltage VF. Herein, the third high voltage VF may be a fourth driving voltage different from the first to the third driving voltages. However, the fourth driving voltage may have a potential difference equal to the second driving voltage, i.e., the gate electrode driving voltage in terms of a potential difference for the third driving voltage, i.e., the cathode electrode driving voltage.

Figure 6:
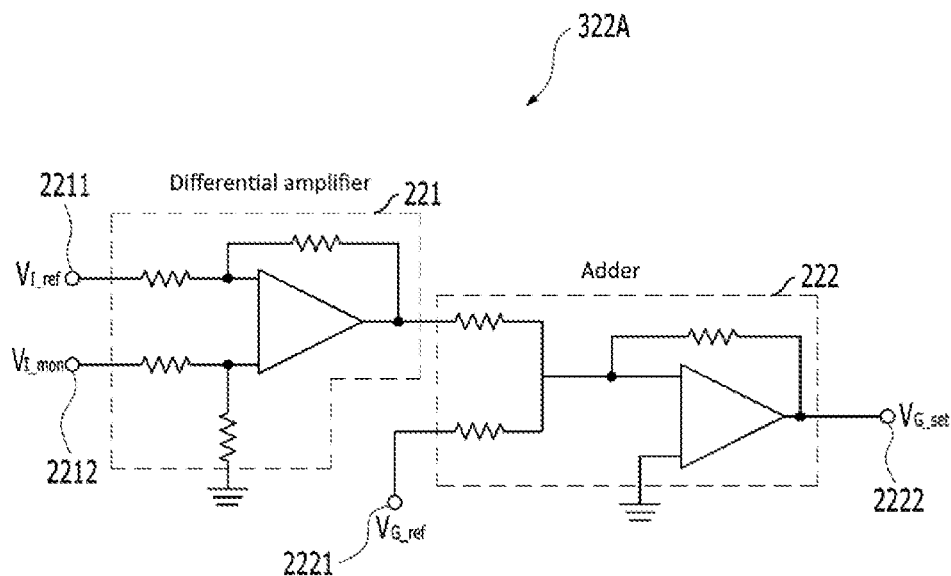
FIG. 6 shows an implementation example of a current controller for the embodiments of FIGS. 3 to 5.

FIG. 6 shows an implementation example of a current controller in the embodiments of FIGS. 3 to 5.

The current controller 322A, according to the implementation example, is configured to adjust the voltage of the driving signal applied to the gate electrode according to the difference between the current value and the preset reference value, which the current value is determined by estimating the current between the first high voltage VH output terminal 331 and the low voltage VL output terminal 333. Here, the current value is a tube current as a feedback signal. This is because the amount of electrons emitted from the cathode electrode depends on the voltage applied to the gate electrode. To achieve this, the current controller 322A may include a differential amplifier 221, and an adder 222. The differential amplifier 221 may include a first input terminal 2211 receiving a current value reference signal and a second input terminal 2212 receiving a tube current monitoring signal and output the same, and may be configured to amplify the difference between the signals of them. The adder 222 is configured to receive the output signal of the differential amplifier 221, add the output signal to the gate voltage reference signal input to the remaining input terminal 2221, and output the adjusted gate voltage setting signal through the output terminal 2222. Herein, according to the output gate voltage setting signal, the voltage converter adjusts the second high voltage VM driving signal.

Figure 7:
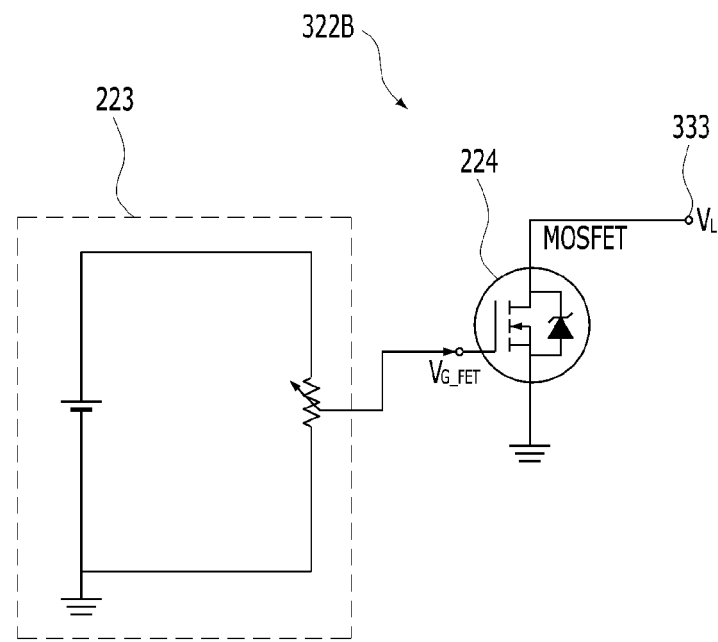
FIG. 7 shows an implementation example of the current controller for the embodiments of FIGS. 3 to 5.

FIG. 7 shows an implementation example of the current controller in the embodiments of FIGS. 3 to 5.

As another implementation example different from the implementation example of FIG. 6, a current controller 322B may include at least one field effect transistor (FET) 224, so as to control the current to flow constantly to an output terminal 333 of the low voltage VL driving signal. In this case, the field effect transistor 224 may include an FET gate control circuit 223 configured to apply an appropriate gate signal to the field effect transistor 224 since the current value flowing between the source and drain terminals changes according to the voltage input to the gate terminal.

In this case, the driving sequence for driving the electric field emission X-ray source is preferably as follows: an ON signal is firstly applied to the gate terminal of the field effect transistor 224 of the current controller 322B; and in this state, the first high voltage VH driving signal for the anode electrode and the second high voltage VM driving signal for the gate electrode are sequentially turned on. The driving sequence may be not limited thereto, but the above driving sequence is advantageous in that it is possible to configure the current controller 322B with a low specification field effect transistor (FET).

Figure 8:
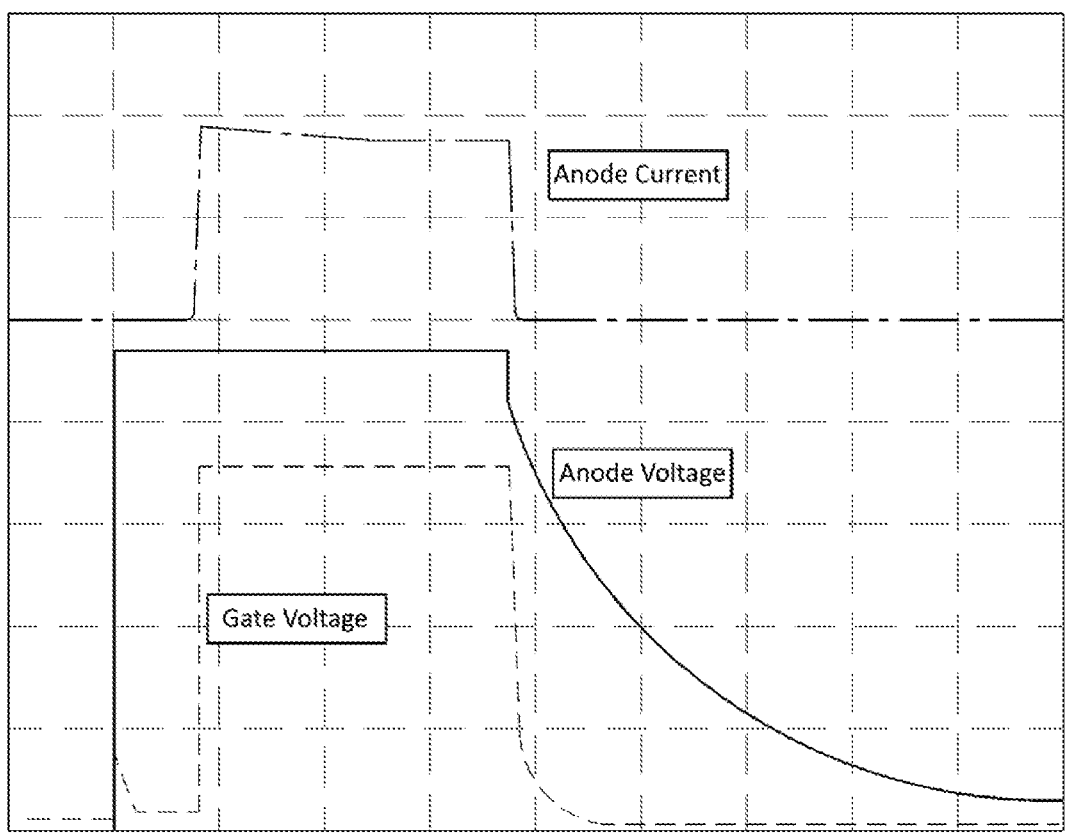
FIG. 8 shows a driving signal applied to an electric field emission X-ray source and a measured waveform of a tube current according thereto in a conventional X-ray generation device.

FIG. 8 shows a driving signal applied to an electric field emission X-ray source and a measured waveform of a tube current according thereto in a conventional X-ray generation device.

As shown in the drawing, when a high voltage (about 65 kV) is applied between the anode electrode and the cathode electrode and then, a gate ON voltage (about 3 kV) is applied to the gate electrode, an electron beam is emitted from the electron emitter disposed in the cathode electrode to form a tube current. Here, the amount of emitted X-rays is proportional to the tube current value. However, the problem is that the tube current (anode current) value gradually decreases from the time when the gate ON voltage is applied and the anode voltage and the gate voltage are maintained constantly. This means that the amount of X-rays in the X-ray generation device decreases with time.

To solve the above problem, in the portable X-ray imaging device according to the present embodiment, more specifically, in the X-ray generation device constituting the portable X-ray imaging device, as described above, when all of the driving signals of the three voltages in the electric field emission X-ray source 44 are turned on, by maintaining the tube current constant, the amount of emitted X-rays per hour is maintained constant.

Figure 9A:
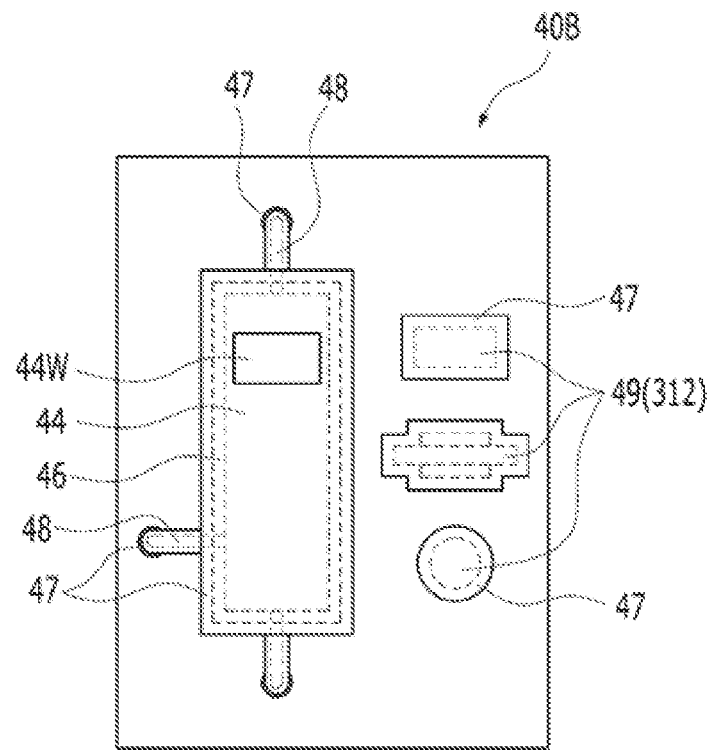
FIGS. 9A and 9B shows an X-ray source unit according to the embodiment of FIG. 4.
Figure 9B:
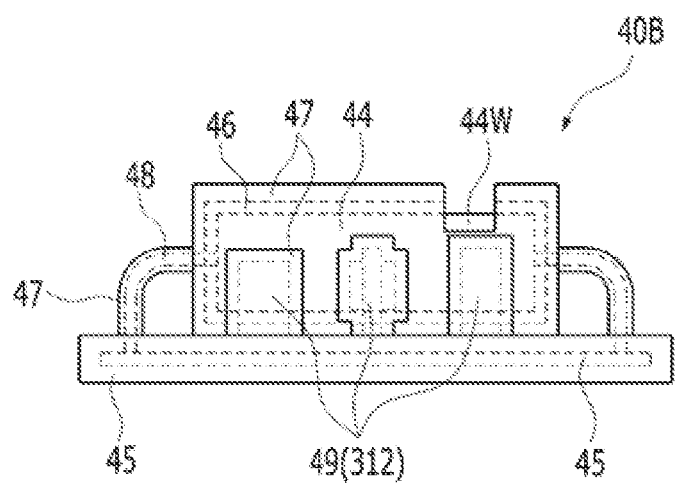

FIGS. 9A and 9B shows an X-ray source unit according to the embodiment of FIG. 4.

The drawing shows the embodiment of FIG. 4. A high voltage component 49 that constitutes the second voltage converter 312 handling the signal of the high voltage state is disposed on a printed circuit board 45 of the X-ray source unit 40B. The X-ray source unit 40B is provided with a second insulation molding 47 surrounding the field emission X-ray source 44 which is implemented on the printed circuit board 45 and surrounded by the first insulation molding together with the high voltage component.

FIG. 9A is a plan view of the X-ray source unit 40B viewed from an X-ray emission window 44W through which X-rays are emitted, and FIG. 9B is a side view of the X-ray source unit 40B viewed from a direction where a plurality of high voltage components 49 are mounted.

The electric field emission X-ray source 44 has the first insulation molding 46 firstly surrounding the surface thereof, wherein electrode leads 48 that are connected to the cathode electrode, the anode electrode, and the gate electrode respectively are exposed to the outside of the first insulation molding 46 and mounted on an electrode pad or the like of the printed circuit board 45. Due to this configuration, it is possible to firstly prevent dielectric breakdown through the body of the electric field emission X-ray source 44. Further, the electric field emission X-ray source 44 with the first insulation molding surrounding therearound along with the second voltage converter 312 mounted to the printed circuit board 45, more specifically, along with the high voltage components 49 constituting the second voltage converter 312 is surrounded again by the second insulation molding 47. Due to this configuration, it is possible to prevent the dielectric breakdown between the high voltage components 49 via the printed circuit board 45 as well as the dielectric breakdown between the electrode leads 48. The first insulation molding 46 may serve as an X-ray shielding layer made of an electrically insulating X-ray shielding material. The first insulation molding 46 may be made of a coating material containing, for example, bismuth oxide. Herein, the coating material containing bismuth oxide means an insulation shielding material in which a bismuth oxide powder is mixed and cured in a resin base material. For reference, the material which is mixed in the form of powder in the resin base material and exhibits the shielding and insulating property is not necessarily limited to bismuth oxide, and it may be replaced with another material as long as it exhibits shielding and insulating properties.

The second insulation molding 47 may be made of an electrically insulating material lighter than the material forming the first insulation molding 46, such as, silicone or epoxy.

Figure 10:
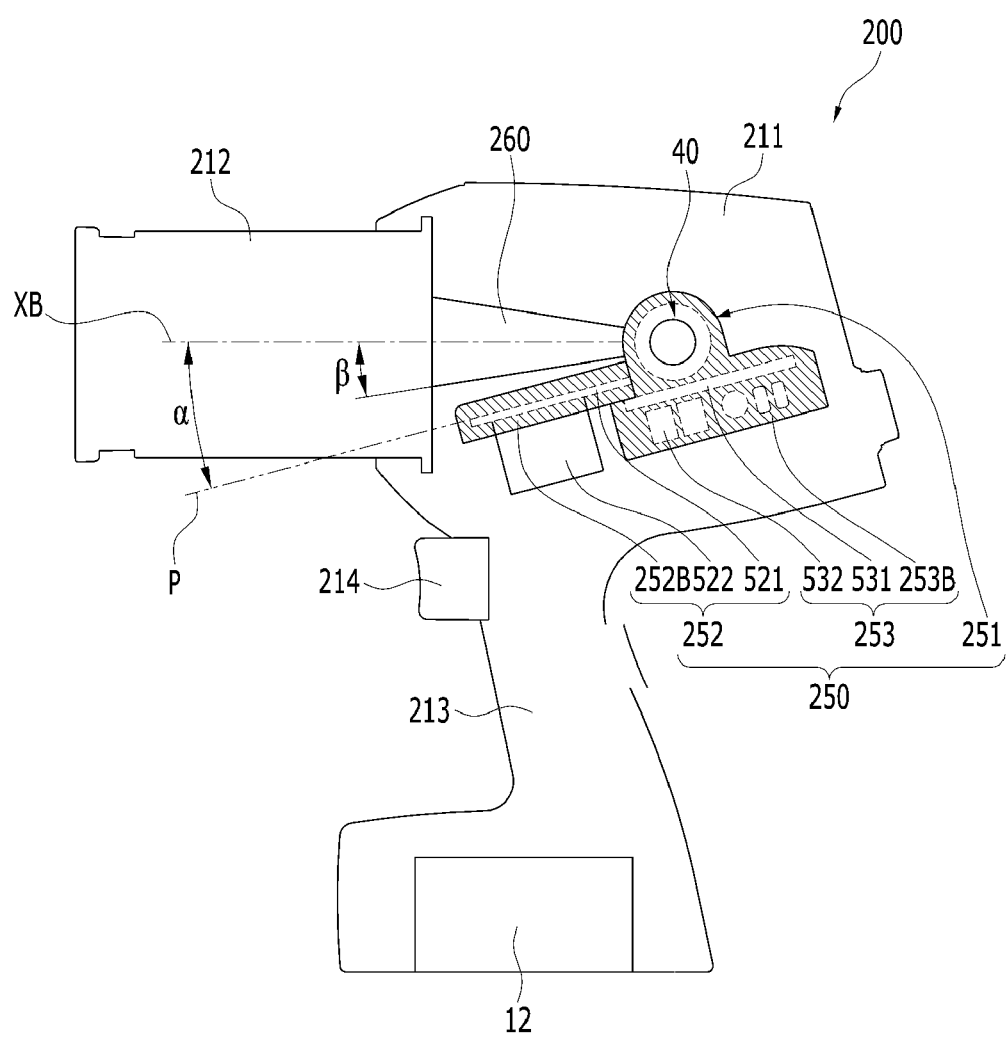
FIG. 10 shows an inner structure of the portable X-ray generation device according to an embodiment of the present invention.

FIG. 10 shows an inner structure of the portable X-ray generation device according to an embodiment of the present invention.

The portable X-ray generation device 200 according to the embodiment includes: a body part 211 with the electric field emission X-ray source 40 mounted therein; a cylindrical collimator 212 disposed at a front of the body part 211; and a grip 213 disposed at the lower portion of the body part 211. The grip 213 may be provided with a trigger type switch 214 at an upper portion thereof, and a rechargeable battery pack 12 at a lower portion thereof. The portable X-ray generation device 200 according to the embodiment may take the form of a hair dryer or an electric drill as a whole.

In the body part 211, the electric field emission X-ray source 40 is not installed solely but is disposed in a frame forming the X-ray source drive assembly 250. The electric field emission X-ray source 40 has a cylindrical shape in a simplified form, and is laid out in a direction perpendicular to the plane of the drawing. In other words, the cylindrical electric field emission X-ray source 40 is disposed in the transverse direction when viewed from the front (the left side of the drawing) in which the X-ray beam XB is emitted. Hereinafter, the direction in which the X-ray beam is emitted from the electric field emission X-ray source 40 to the outside is referred to as forward, and the opposite direction is expressed as rearward.

In the above mentioned frame, an X-ray source accommodation part 251 with the electric field emission X-ray source 40 mounted therein may be formed in a cylindrical shape to correspond to an outer circumferential surface of the electric field emission X-ray source 40. The X-ray source drive assembly 250 includes: a first driving circuit 252 extending diagonally from the X-ray source accommodation part 251 forward and downward; and a second driving circuit 253 extending diagonally from a lower portion the X-ray source accommodation part 251 backward and upward. In the first driving circuit 252, a first printed circuit board 521 constituted by a first voltage step-up circuit including a first step-up transformer 522 is disposed, and in the second driving circuit 253, a second printed circuit board 531 provided with a second step-up transformer 532 including a plurality of diodes and a capacitor is disposed. The electric field emission X-ray source 40 may be disposed at the upper portion of the second printed circuit board 531 to be overlapped therewith.

Herein, the first driving circuit 252 and the second driving circuit 253 constitute the driving signal generator 30C in the embodiment of FIG. 5, and the first voltage step-up circuit including the first step-up transformer 522 may correspond to the first voltage converter 311C, and the second step-up transformer 532 including the plurality of diodes and the capacitor may correspond to the second voltage converter 312C.

In the X-ray source drive assembly 250, the frame forming the outer shape of the X-ray source drive assembly surrounds the upper and side surfaces of the X-ray source drive assembly, and the lower portion thereof is open. The upper and lower portion of the first printed circuit board 521 and the second printed circuit board 531, and the periphery of the electric field emission X-ray source 40 are filled with an insulating filler such as silicone to form insulation molding parts 251B, 252B, and 253B as indicated by hatched areas in the drawing. Meanwhile, not shown in the drawing, in the X-ray source accommodation part 251, a window is formed at a position where X-rays are emitted toward the front such that a part of the electric field emission X-ray source 40 including an X-ray emitting portion is exposed. Further, the surface of the electric field emission X-ray source 40 is surrounded by the X-ray shielding layer except from a portion corresponding to the window, thereby preventing undesirable X-ray emission.

An X-ray emission cone 260 is disposed between the X-ray source accommodation part 251 and the cylindrical collimator 212 in front of the electric field emission X-ray source 40. The X-ray emission cone 260, which is a cone-shaped structure, may be made of an X-ray shielding material or may include at least an X-ray shielding layer. The X-rays emitted from the electric field emission X-ray source 40 is in an X-ray beam within a predetermined angle range while passing through the X-ray emission cone 260. The cylindrical collimator 212 is also provided with an X-ray shielding layer on an inner or outer wall thereof to block X-rays traveling in unintended directions due to diffused reflection or the like, and controls the irradiation range of the X-ray beam. Meanwhile, in order to control the shape of the X-ray beam as required, an X-ray shielding structure having a fixed or variable opening, such as a square or a linear opening, may be provided in front of the cylindrical collimator 212.

Reference will now be made to the inside of body part 211 of the portable X-ray generation device 200 according to the embodiment in terms of space utilization and structure placement. The X-ray emission cone 260 is arranged such that the center line thereof coincides with the center line XB of the cylindrical collimator 212. As a result, the center line XB is the centerline of the X-ray beam emitted therethrough. Meanwhile, the first driving circuit 252 is disposed at the lower portion of the X-ray emission cone 260, and the plane P to which the first printed circuit board 521 belongs is arranged to be inclined by angle α with respect to the horizontal plane including the center line XB. The angle α is greater than or equal to the angle β, which is the slope angle of the outer wall of the X-ray emission cone 260 for the center line XB. As the value of the angle α approaches the value of the angle β, the first driving circuit 252 including the first printed circuit board 521 can be brought closer to the X-ray emission cone 260, which is advantageous for efficient utilization of the internal space of the body part 211. This means that it is advantageous to miniaturize the device.

The X-ray source drive assembly 250 may be indicated as having a predetermined angle with the center line XB of the X-ray emission cone 260. Thereby, while the electric field emission X-ray source 40 is as close as possible to the first printed circuit board 521, the predetermined X-ray emission range and the X-ray source drive assembly 250 can be prevented from interfering with each other.

Herein, reference will be made to characteristics of the electric field emission X-ray source 40, and the first driving circuit 252 and the second driving circuit 253. As described above, the electric field emission X-ray source 40 is constituted by at least triode structure of the cathode electrode, the gate electrode, and the anode electrode. For example, describing with the triode structure, based on the voltage applied to the cathode electrode, a first high voltage with a potential difference of about 65 kV is applied as an electron acceleration voltage to the anode electrode, and a second high voltage with a potential difference of about 5 to 10 kV is applied as a switching signal to the gate electrode. The driving voltage level allows the portable X-ray generation device according to the present invention to meet the tube voltage specification of the medical X-ray generation device. However, the present invention is not limited thereto.

The first driving circuit 252 serves as a first step-up transformer, and the second driving circuit 252 serves as a second step-up transformer. The first driving circuit 252 firstly boosts, for example, the predetermined direct current power or AC power converted through an inverter circuit to generate a first driving voltage of about 5 to 10 kV. To achieve this, the first driving circuit 252 includes the first printed circuit board 521 with the first step-up transformer 522 mounted thereto. The first printed circuit board 521 is provided with an electrode pattern constituting a circuit by connecting the first printed circuit board and various other components, and among these, the first step-up transformer 522, i.e., the transformer has the largest volume and weight. The first step-up transformer 522 is configured such that a portion of the electrode close to the substrate is covered by the insulating filler forming the insulation molding part 252B together with the electrode pattern on the first printed circuit board 521 and low-height elements, and a portion above that portion is exposed outside the insulation molding part 252B.

The first driving voltage generated in the first driving circuit 252 is supplied as a switching signal to the gate electrode of the electric field emission X-ray source 40, and also supplied to the second driving circuit 253 to generate the anode electrode driving signal through the second boost. In second printed circuit board 531 including the second driving circuit 253, the second step-up transformer 532 constituted by a plurality of diodes and a capacitor is provided. The second step-up transformer 532 is also called as a voltage multiplier circuit, and may be configured as an n-fold voltage rectifier circuit or a Cockroft voltage doubler rectifier circuit that boosts the input voltage to n times the voltage. This allows the first driving voltage to rise to a second driving voltage of about 65 kV, the anode electrode driving voltage of the electric field emission X-ray source 40. The boosted second driving voltage is supplied from the output terminal on the second printed circuit board 531 to the anode electrode of the electric field emission X-ray source 40 disposed close to the upper portion of the output terminal. Meanwhile, most of the devices constituting the second printed circuit board 531 and the second step-up transformer 532 may be all buried in an insulating filler to form another insulation molding part 253B. As described above, since the second driving circuit 253 handles a higher voltage of several tens of kV compared to the first driving circuit 252, and complete covering the circuit with the insulating filler is preferable for the insulating stability and the lifetime.

The portable X-ray generation device 200 according to the embodiment has the following features in terms of weight reduction. First, as an X-ray source, an electric field emission X-ray source 40 is used to reduce the weight of the X-ray source to 20 to 150 g, more specifically to 20 to 50 g, preferably about 40 g. The X-ray shielding layer surrounding the surface of the X-ray source was also coated with a lightweight X-ray shielding material such as bismuth oxide.

Second, the driving circuit generating driving signals of the electric field emission X-ray source 40 is divided into the first driving circuit 252 handling a low voltage, and the second driving circuit 253 handling a high voltage, wherein the deeper insulation molding part 253B is formed on the second driving circuit 253 side, where more stable insulation performance is required, and the shallow insulation molding part 252B is formed on the first driving circuit 252 side to cover the first printed circuit board 521 and its electrode pattern, thereby reducing the weight increase by the insulating filler.

Third, in the cylindrical collimator 212 and the X-ray emission cone 260, the structure is formed of lightweight synthetic resin, and a lightweight X-ray shielding material such as bismuth oxide is laminated on the outer wall of the structure to form an X-ray shielding layer, thereby achieving weight reduction of the device.

In particular, the above weight reduction is achieved without degrading the output of the portable X-ray generation device. The weight of the portable X-ray generation device using the electric field emission X-ray source according to the embodiment may be 0.8 kg to 3 kg, more specifically, 1.0 to 2 kg including about 350 g as the weight of a separate additional configuration such as additional back shields (X-rays shielding structure for protecting the user from X-rays scattered backward and emitted), preferably, about 1.83 kg. In this case, under the condition of the power supply, the driving voltage, the tube current, and the like, the x-ray emission output may be 120W to 300W, more specifically, about 150 to 250W, preferably, 200W. Accordingly, the output per unit weight of the portable X-ray generation device may be 40 to 375 (W/kg), more specifically, 50 to 150 (W/kg). As a preferred embodiment, when the device weighs 1.83 kg and the output is 200 W, the output per unit weight is about 109 (W/kg).

Meanwhile, looking at the portable X-ray generation device 200 in terms of miniaturization, the first driving circuit 252 with the bulky first step-up transformer 522 mounted thereto is disposed toward the front of the electric field emission X-ray source 40, and a lower space secured by tilting the first printed circuit board 521 at the angle along the outer angle of the X-ray emission cone 260 is utilized. Further, the first printed circuit board 521 and the second printed circuit board 531 are arranged at different heights with respect to the electric field emission X-ray source 40, and the first printed circuit board 521 is disposed at a relatively higher height so as to further secure a space below the first printed circuit board 521.

In the embodiment, the cylindrical electric field emission X-ray source 40 may 10 to 40 mm in diameter, and 40 to 70 mm in length, more specifically, 10 to 30 mm in diameter, and 40 to 70 mm in length, preferably, about 15 mm in diameter, and about 57.5 mm in length. Under the condition of the tube current of 2 to 3 mA and the tube voltage of 55 to 75 kV between the cathode electrode and the anode electrode, the X-ray emission time is controlled in the range of 0.01 to 3 sec, and the focal size of the X-ray emission point is 0.2 to 1 mm. To be more specific, the tube current is 2.5 mA, the tube voltage is 60 kV or 65 kV, the focal size is 0.4 mm, and the X-ray emission time is 0.05 to 0.5 sec.

Figure 11:
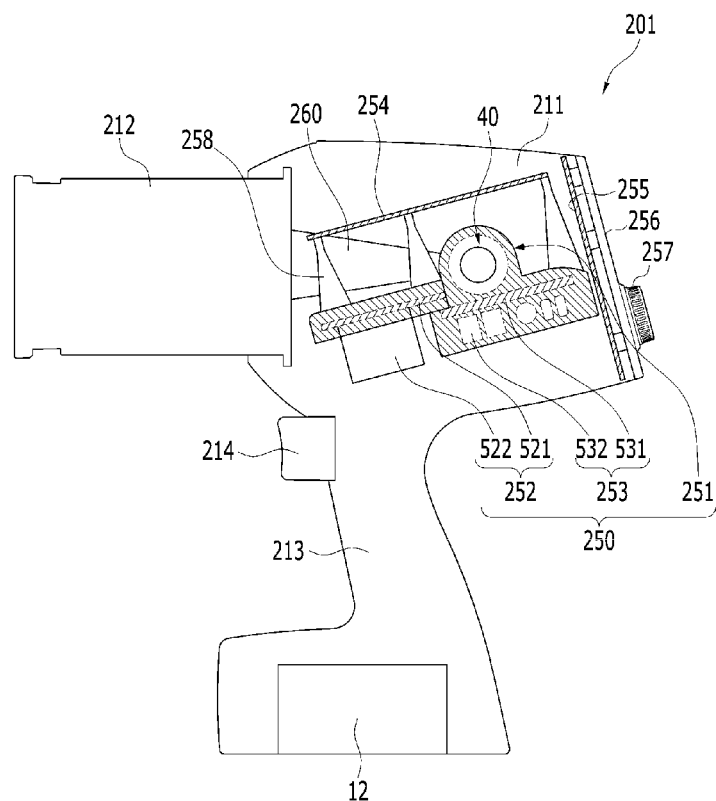
FIG. 11 shows an inner structure of the portable X-ray generation device according to an embodiment of the present invention.

FIG. 11 shows an inner structure of the portable X-ray generation device according to an embodiment of the present invention.

The portable X-ray generation device 201 according to the embodiment includes the configuration of the portable X-ray generation device 200 according to the embodiment of FIG. 10, particularly, all the configuration of the X-ray source drive assembly 250. Accordingly, herein, the redundant description will be omitted and only the added configuration will be described.

The device 201 according to the embodiment may further include: a bracket structure 258 built by avoiding X-ray emission cone 260 on the upper portion of the frame of the X-ray source drive assembly 250; and a third printed circuit board 254 fixed to the bracket structure 258. The third printed circuit board 254 may include an inverter circuit for converting the power supplied from the battery pack 12, which is the direct current power, into AC. No separate insulation molding is required for the third printed circuit board 254.

Further, in the embodiment, a fourth printed circuit board 255 may be disposed at the back of the X-ray source drive assembly 250. The fourth printed circuit board 255 may include a control circuit configured to display the operating status of the device by being connected with a control panel 256 including a user interface 257 and control the operation mode, and the like. Not shown in the drawing, the fourth printed circuit board 255 may be also coupled to the frame of the X-ray source drive assembly 250 through the bracket structure. The fourth printed circuit board and the control panel are disposed at the upper portion of the third printed circuit board 254, but they may be disposed toward the side of the body part 211.

Figure 12:
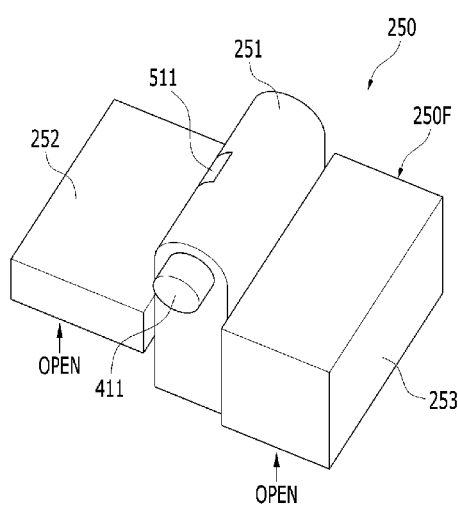
FIG. 12 shows an example of an X-ray source drive assembly in the embodiment of FIG. 10 or FIG. 11.

FIG. 12 shows an example of an X-ray source drive assembly in the embodiment of FIG. 10 or FIG. 11.

This drawing shows the X-ray source drive assembly 250 described with reference to FIG. 10 as viewed from the upper rear side thereof. There is an X-ray source accommodation part 251 in the center, and an open window 511 is seen in the middle. On one side of the X-ray source accommodation part 251, to release the heat generated from the anode electrode of the electric field emission X-ray source disposed thereinside to the outside, a heat sink 411 protruding out of the frame 250F may be disposed. The heat sink 411 may be formed of a ceramic material that is electrically insulating material and has excellent thermal conductivity. In the X-ray source drive assembly 50, the frame 250F is formed of a synthetic resin material so as to surround the upper surface and the side surface except the window 511 and the heat sink 411 and to open the lower surface thereof.

Figure 13:
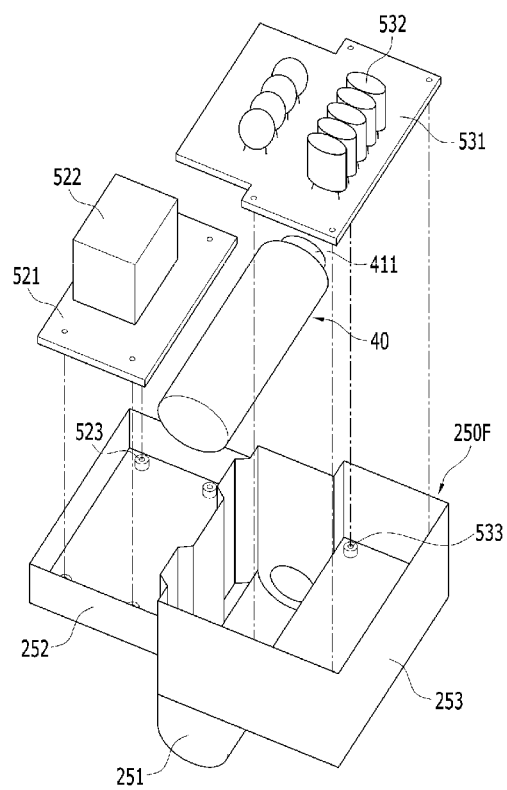
FIG. 13 shows an exploded perspective view of the X-ray source drive assembly of FIG. 12 when viewed from the opposite direction.

FIG. 13 shows an exploded perspective view of the X-ray source drive assembly of FIG. 12 when viewed from the opposite direction.

In this drawing, to help understand the inner structure of the frame 250F, an insulating filler for an insulating molding is not shown. As described above with reference to FIG. 10, in the frame 250F, the portion corresponding to the first driving circuit 252 is formed to be shallow, and the portion corresponding to the second driving circuit 253 is formed to be deep. Further, X-ray source accommodation part 251 is formed deeper inside the portion corresponding to the second driving circuit 253. In the frame 250F, inside the first driving circuit 252, a plurality of boss structures 523 for seating and fixing the first printed circuit board 521 are provided, and also inside the second driving circuit 253, a plurality of boss structures 533 for seating and fixing the second printed circuit board 531 are provided. Further, not shown in the drawing, inside the X-ray source accommodation part 251, a three-dimensional structure may be provided to support a part of the electric field emission X-ray source 40. The plurality of boss structures 523 and 533 respectively form a space for injection of an insulating filler in a fluid state with each of the first printed circuit board 521 and the second printed circuit board 531 is fixed, so that opposite surfaces of the first and second printed circuit boards 521 and 531 are filled with the insulating filler.

As the insulating filler, for example, an epoxy or a silicone resin may be used. The first printed circuit board 521, the second printed circuit board 531, and the electric field emission X-ray source 40 connected to each other by wiring are disposed the inner space of the frame 250F, and a fluid epoxy or silicone resin is injected thereon. In the frame 250F, when an epoxy or a silicone resin is filled and cured at an intended depth according to the sidewall height or the like of the portion that accommodates each of these portions, the insulation molding parts 252B and 253B are formed.

Figure 14:
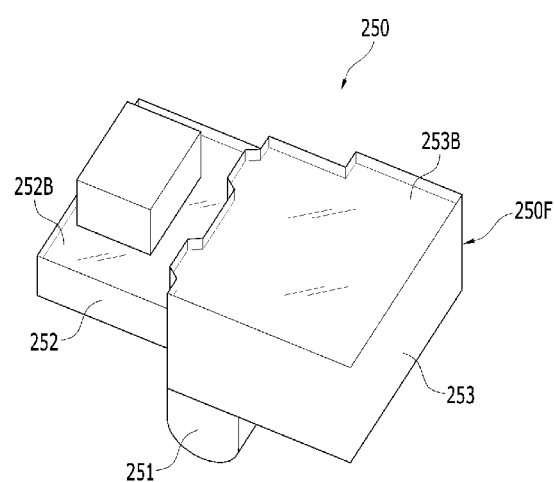
FIG. 14 shows a perspective view of the X-ray source drive assembly of FIG. 12 when viewed from the opposite direction.

FIG. 14 shows a perspective view of the X-ray source drive assembly of FIG. 12 when viewed from the opposite direction.

As shown in the drawing, the insulation molding part 252B in the first driving circuit 252 is formed to have a shallow depth to the extent that it covers both sides of the first printed circuit board and small-size elements mounted on the surface thereof, and as a result, the electrode portion of the first step-up transformer 522 is immersed in the insulation molding part 252B, and a part of the opposite side thereof is exposed to the outside. Meanwhile, the insulation molding part 253B in the second driving circuit 253 is formed deep enough to cover both the second printed circuit board 531 shown in FIG. 13 and the second step-up transformer 532 mounted thereon. As shown in the drawing, the depth of the insulation molding parts 252B and 253B may be implemented differently depending on the sidewall height of the corresponding part of the frame 250F. In other words, in the frame 250F, the side wall surrounding the second driving circuit 253 may be formed higher than the side wall surrounding the first driving circuit 252 from the respective bottom surfaces.

Figure 15:
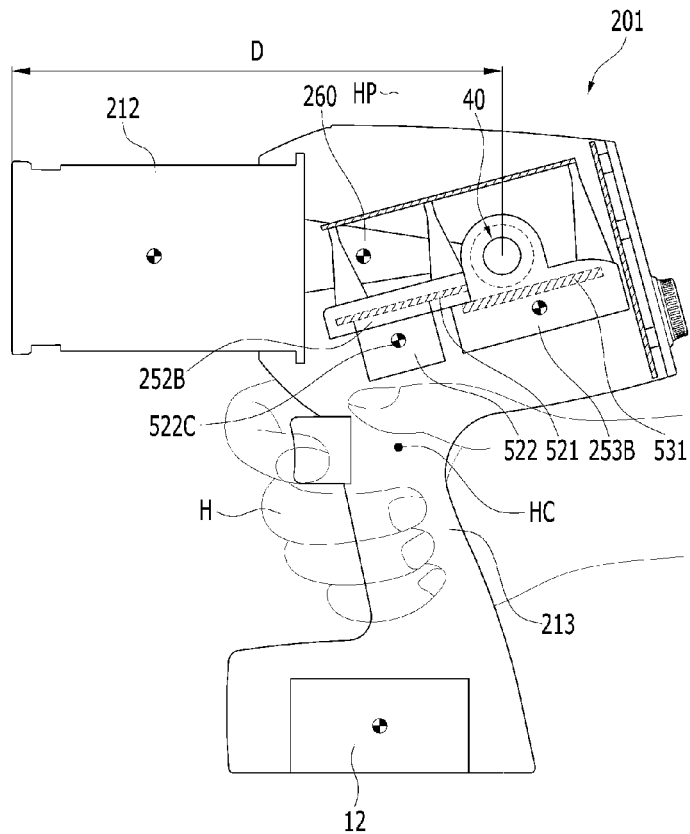
FIG. 15 shows the inner structure of the portable X-ray generation device according to the embodiment of FIG. 11 in terms of weight distribution.

FIG. 15 shows the inner structure of the portable X-ray generation device according to the embodiment of FIG. 11 in terms of weight distribution.

The portable X-ray generation device 201 according to the embodiment is designed to be used while the user holds the grip 213 with one hand H and use the device while handles the weight of the device. According to the embodiment, to achieve this, in addition to reduction of the weight of the major parts, it is possible to balance the device itself without applying extra force through proper weight distribution of front/rear, top/bottom, and left/right. One of the technical features of the present invention is that the placement of parts in consideration of weight distribution does not go against the downsizing of the device.

There is a restriction requirement on the placement of components within the device that must be observed, that is, a distance D from the front end of the cylindrical collimator 212 to the center of the electric field emission X-ray source 40, which is the distance from the focus where the X-ray beam is emitted to the place where X-ray beam is in the outside of the device, should be 200 mm or more. The cylindrical collimator 212 serves to shield the uncontrolled X-ray beam from being emitted from the inside thereof, and the X-ray emission cone 260 disposed between the cylindrical collimator 212 and the electric field emission X-ray source 40 controls the X-rays emitted in a wide range in a beam shape of a certain angle range, so it includes an X-ray shielding layer of X-ray shielding material containing lead or bismuth oxide. This X-ray shielding layer is a factor in increasing the weight of the component.

The centers of gravity of the cylindrical collimator 212 and the X-ray emission cone 260 are located forward relative to the center line HP of the grip 213. The balance with the weights is the insulation molding part (253B) with the second printed circuit board 531 disposed therein. This is because the insulating filler filling between them as well as a plurality of diodes and the capacitor is heavy. Of course, since the electric field emission X-ray source 40 itself is constituted by a metal electrode and a ceramic spacer, it acts as a weighting part behind the center line HP.

Meanwhile, the first step-up transformer 522 is another component that weighs heavy. This is because the first step-up transformer 522 has a large amount of copper wire wound around it. According to the embodiment, the first step-up transformer 522 may be disposed at a position where the center line HP of the grip 213 passes therethrough. To be more specific, the center of gravity 522C of the first step-up transformer 522 may be positioned on the center line HP. Further, at the lower portion of the grip 213, the battery pack 12 may be also disposed at a position where the center line HP of the grip 213 passes therethrough. The closer the components that occupy a high proportion of the weight of the device are on or near the centerline HP of the grip 213 gripped by the user's hand H, it is easy to maintain balance. Meanwhile, the inverter circuit or the control circuit may be located somewhat farther from the center line HP because it is relatively light in weight.

Figure 16:
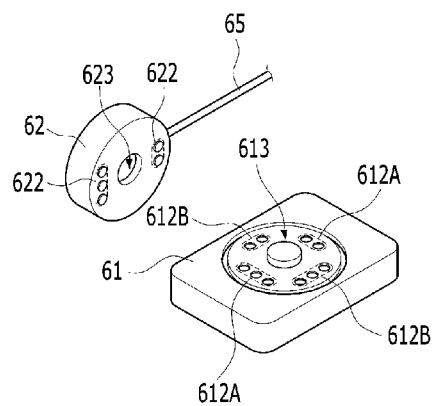
FIG. 16 shows an example of an X-ray sensor unit in the embodiment of FIG. 1 or FIG. 2.

FIG. 16 shows an example of an X-ray sensor unit in the embodiment of FIG. 1 or FIG. 2.

As described above, the X-ray source is constituted by the sensor portion 61, and the connection portion 62, wherein the connection portion 62 and the sensor portion 61 may be electrically connected to each other through a plurality of channels via connection terminal groups 622, 612A, and 612B constituted by a plurality of connection terminals. The plurality of channels may include a power supply channel as well as a communication channel transmitting the imaging data generated from the sensor portion 61. Meanwhile, the connection portion 62 may be coupled in two or more different directions with respect to the sensor portion 61. The connection here also includes the meaning of electrical connection. For example, to couple the connection portion 62 and the sensor portion 61 in two different directions, one connection terminal group 622 may be disposed in the connection portion 62, and two connection terminal groups 612A and 612B, which are folioed corresponding to the one connection terminal group 622 and are selectively connected, may be disposed in the sensor portion 61.

Further, the connection portion 62 and the sensor portion 61 may be connected by near field communication (NFC) modules 613 and 623. The connection portion 62 and the sensor portion 61 may be connected to transmit and receive power and imaging data to each other with only the near field communication modules 613 and 623, or may be connected to the connection means through a plurality of connection terminal groups 622, 612A and 612B in combination with the near field communication modules 613 and 623.

INDUSTRIAL APPLICABILITY

The portable X-ray generation device according to the present invention can be used not only as part of a diagnostic system for intra-oral X-ray imaging in dentistry but also as part of an X-ray imaging system for nondestructive testing of products or equipment.

The invention claimed is:

1. A portable X-ray generation device comprising:
    an electric field emission X-ray source including a cathode electrode having an electron emitter, an anode electrode having an X-ray target surface, and a gate electrode disposed between the cathode electrode and the anode electrode; and
    a driving signal generator configured to generate at least three driving signals applied to the cathode electrode, the anode electrode, and the gate electrode, respectively, by using a direct current power having a predetermined voltage, wherein the driving signal generator includes a current controller configured to maintain a tube current between the anode electrode and the cathode electrode to have a constant value during X-ray emission, wherein the driving signal generator includes a voltage converter configured to generate a first driving voltage of a first voltage level (V1) for the anode electrode, a second driving voltage of a second voltage level (V2) for the gate electrode, and a third driving voltage of a third voltage level (V3) for the cathode electrode by using the direct current power, and the first to third voltage levels (V1, V2, and V3) have relations of V1>V2>V3, and wherein the driving signal generator includes:
a first voltage converter configured to generate the second driving voltage by firstly boosting a voltage of the direct current power to the second voltage level (V2); and
a second voltage converter configured to generate the first driving voltage by secondly boosting the second voltage level to the first voltage level (V1).

2. The portable X-ray generation device of claim 1, wherein a voltage of the direct current power is 5V to 30V, the first driving voltage has a potential difference of 55 kV to 75 kV for the third driving voltage, and the second driving voltage has a potential difference of 0.5 kV to 20 kV for the third driving voltage.

3. The portable X-ray generation device of claim 2, wherein the electric field emission X-ray source further includes a focusing electrode disposed between the gate electrode and the anode electrode,
the driving signal generator further generates a fourth driving voltage for the focusing electrode to apply the same to the focusing electrode, and
the fourth driving voltage has a potential difference of 0.5 kV to 20 kV for the third driving voltage.

4. The portable X-ray generation device of claim 1, wherein the first voltage converter includes a coil transformer, and
the second voltage converter includes a voltage multiplier circuit using a plurality of diodes and a capacitor.

5. The portable X-ray generation device of claim 1, further comprising:
a first insulation molding configured to surround a part or all of the electric field emission X-ray source and also serve as an X-ray shielding layer;
a printed circuit board with the electric field emission X-ray source mounted thereto; and
a second insulation molding configured to surround parts or all of the electric field emission X-ray source with the first insulation molding and the printed circuit board.

6. The portable X-ray generation device of claim 5, wherein the driving signal generator includes:

a first voltage converter configured to generate a second driving voltage of a second voltage level (V2) by firstly boosting a voltage of the direct current power; and
a second voltage converter configured to generate a first driving voltage of a first voltage level (V1) by secondly boosting the second voltage level,
wherein the second voltage converter is mounted to the printed circuit board, and the second insulation molding surrounds a part or all of the second voltage converter.

7. The portable X-ray generation device of claim 1, wherein the current controller adjusts a voltage of the driving signal applied to the gate electrode according to the difference between a feedback signal of the tube current value and a set value.

8. The portable X-ray generation device of claim 1, wherein the current controller includes at least one field effect transistor configured to be connected to the cathode electrode and maintain a current value applied during X-ray emission constant.

9. The portable X-ray generation device of claim 8, wherein the driving signal generator is configured to sequentially turn on the driving signal for the anode electrode and the driving signal for the gate electrode in a state where an ON signal is applied to a gate terminal of the field effect transistor of the current controller.

10. The portable X-ray generation device of claim 1, further comprising:
a main body with the electric field emission X-ray source and the driving signal generator mounted thereto; and
a grip rotatably and tiltably coupled to a side of the main body via a freely rotating joint.

11. The portable X-ray generation device of claim 10, further comprising a battery accommodated in the grip and configured to supply the direct current power.

12. The portable X-ray generation device of claim 11, further comprising an external power adapter configured to supply the direct current power.

13. The portable X-ray generation device of claim 1, further comprising:
a main body with the electric field emission X-ray source and the driving signal generator mounted thereto; and
a holder rotatably and tiltably coupled to a side of the main body via a freely rotating joint.

14. The portable X-ray generation device of claim 1, further comprising:
a main body with the electric field emission X-ray source and the driving signal generator mounted thereto; and
an X-ray sensor connected with the main body via a cable and configured to provide imaging data by receiving X-rays emitted from the electric field emission X-ray source and transmitted through a subject.

15. The portable X-ray generation device of claim 14, further comprising a wireless communication module configured to wirelessly transmit the imaging data of the X-ray source or image data obtained by reconstructing the imaging data.

* * * * *